US012691237B2

(12) United States Patent
Mezzoli et al.

(10) Patent No.: US 12,691,237 B2
(45) Date of Patent: Jul. 28, 2026

(54) DOME-SHAPED LIQUID DISPENSER FOR MEDICAL USES

(71) Applicants: Giorgio Mezzoli, Lugo (IT); Maria Rani, Lugo (IT)

(72) Inventors: Giorgio Mezzoli, Lugo (IT); Maria Rani, Lugo (IT)

( * ) Notice: Subject to any disclaimer, the term of this patent is extended or adjusted under 35 U.S.C. 154(b) by 963 days.

(21) Appl. No.: 17/791,384

(22) PCT Filed: Dec. 31, 2020

(86) PCT No.: PCT/IB2020/062581
§ 371 (c)(1),
(2) Date: Jul. 7, 2022

(87) PCT Pub. No.: WO2021/140413
PCT Pub. Date: Jul. 15, 2021

(65) Prior Publication Data
US 2023/0041960 A1     Feb. 9, 2023

(30) Foreign Application Priority Data
Jan. 8, 2020    (IT) ........................ 102020000000148

(51) Int. Cl.
*A61M 15/08*     (2006.01)
*A61M 11/00*     (2006.01)
(Continued)

(52) U.S. Cl.
CPC .......... *A61M 15/08* (2013.01); *A61M 11/008* (2014.02); *B05B 1/26* (2013.01); *B05B 11/047* (2013.01)

(58) Field of Classification Search
CPC .......... A61M 15/08; A61M 2210/0618; B05B 1/341; B05B 1/3421; B05B 1/3426;
(Continued)

(56) References Cited

U.S. PATENT DOCUMENTS 1,261,282 A * 4/1918 Peabody ............... B05B 1/3436
     239/491
2,135,052 A * 11/1938 Rose ...................... A61H 35/04
     604/24
(Continued)

FOREIGN PATENT DOCUMENTS

CN    110680726 A * 1/2020 ........... A61M 11/02
DE    2625496 A1 * 12/1977
(Continued)

OTHER PUBLICATIONS

International Search Report and Written Opinion in corresponding International Patent Application No. PCT/IB2020/062581 mailed Mar. 31, 2021 (3 pages).

*Primary Examiner* — William R Carpenter
(74) *Attorney, Agent, or Firm* — Leason Ellis LLP

(57) ABSTRACT

A liquid nebulizer (1) for medical uses wherein a dome-shaped body (10) is shaped symmetrically with respect to a first frontal median plane (M) and to a second sagittal median plane (N) intersected in a central axis (A); the dome-shaped body (10) being developed along the axis (A) between a base portion (100) and an upper truncated portion (102) provided with a cavity (1020); at least two channels (12)(12') being provided, each of which shaped to access the cavity (1020) through a respective hole (120)(120') arranged at a given distance from one of the first frontal median plane (M) and second sagittal median plane (N).

15 Claims, 4 Drawing Sheets

(51) Int. Cl.
    *B05B 1/26*           (2006.01)
    *B05B 11/04*        (2006.01)

(58) Field of Classification Search
    CPC ... B05B 1/3431; B05B 1/3436; B05B 1/3463;
                                 B05B 1/3478
    See application file for complete search history.

(56)                        References Cited

U.S. PATENT DOCUMENTS 2,378,348 A  *  6/1945  Wilmes ................. B05B 1/3436
                                        239/491
4,660,555 A      4/1987  Payton

FOREIGN PATENT DOCUMENTS

| | | | | |
|---|---|---|---|---|
| EP | 0319501 A2 | * | 6/1989 | .......... A61M 3/0262 |
| GB | 2466631 A | | 7/2010 | |
| GB | 2525752 A | * | 11/2015 | .......... B05B 1/3463 |
| WO | 9629044 A1 | | 9/1996 | |
| WO | 2009100383 A2 | | 8/2009 | |
| WO | 2016001926 A1 | | 1/2016 | |
| WO | 2016075433 A1 | | 5/2016 | |
| WO | WO-2018025139 A1 | * | 2/2018 | .............. B05B 1/34 |
| WO | 2020064612 A1 | | 4/2020 | |

* cited by examiner

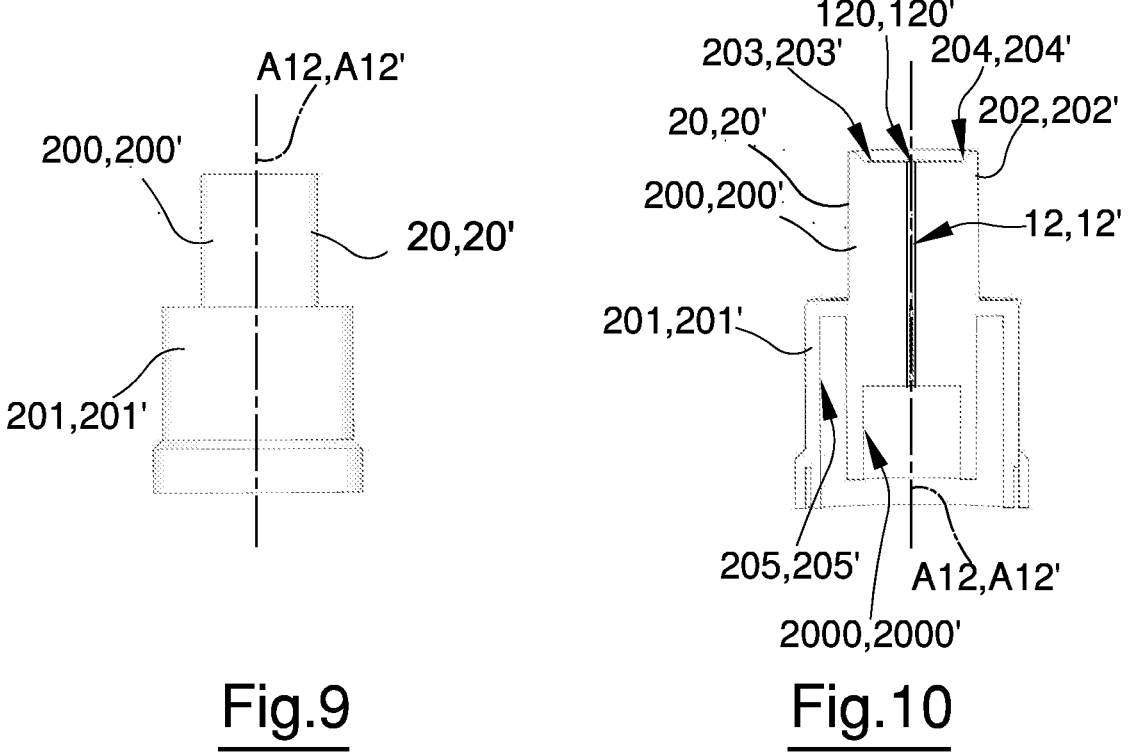
Fig.9
Fig.10
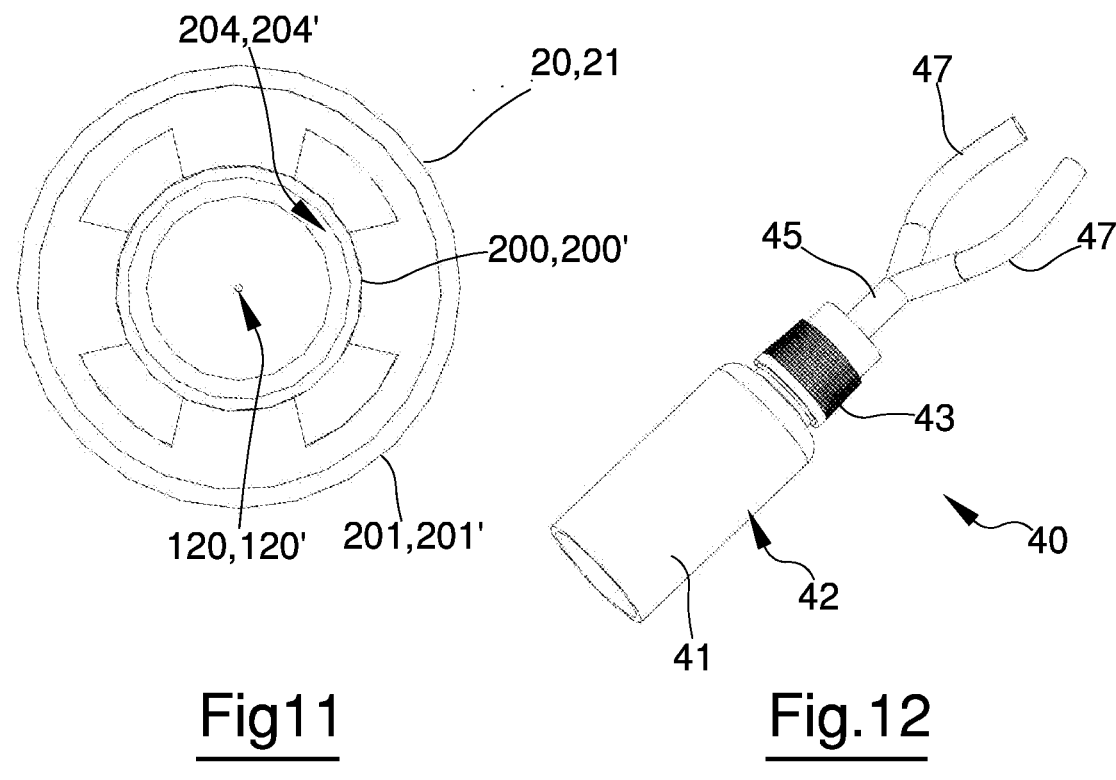
Fig11
Fig.12

DOME-SHAPED LIQUID DISPENSER FOR MEDICAL USES

CROSS-REFERENCE TO RELATED PATENT APPLICATIONS

This patent application is a U.S. National Phase application under 35 U.S.C. § 371 of International Patent Application No. PCT/IB2020/062581, filed on Dec. 31, 2020, which claims priority from Italian patent application no. 102020000000148, filed on Jan. 8, 2020, the entire disclosure of which is incorporated herein by reference.

DESCRIPTION

The present invention concerns a dispenser. In particular, the present invention concerns a dispenser comprising a dome-shaped body to ease the insertion thereof in human or animal body cavities. In further detail, the present invention concerns a pressure-operated dispenser comprising a dome-shaped body to ease the insertion thereof in human or animal body cavities and provided with a nozzle in apical position to spray liquid in nebulized form inside the human or animal body cavities.

DESCRIPTION OF THE STATE OF THE ART

The sector of dispensers of medicated or pharmacologically active solutions includes a huge variety of products, and comprises dispensers that can be used for applying said solutions in nebulized form inside human or animal body cavities, including the nasal cavities, the oral cavity, the vaginal cavity and the outer ear canal, without minimizing the multiple uses of said dispensers. A large part of said dispensers have been conceived and designed to administer solutions in nebulized form inside nasal cavities and have a frustoconical shape.

The nasal cavities form the uppermost part of the respiratory tract and are separated by the nasal septum, which is an osteo-cartilaginous wall coated by mucosa. Each cavity is split into areas having different anatomical shapes according to their natural functions. A summary description of these areas is provided below.

The area of the nasal vestibule is the outermost part of the nose. The nasal vestibule is medially delimited by a rigid component, the nasal septum, and delimited laterally and at the top by an elastic component, the wings of the nose. The structures that compose the nasal vestibule give it the shape of an oval or elliptical funnel, the coronal section area of which tapers from the outside towards the inside. The nasal vestibule has the function of conveying the air inhaled towards the nasal cavity.

The valve area: the nasal valve or ostium internum is the transition point between the nasal vestibule and the nasal cavity. The upper part of the valve area is called nasal valve, and consists of the junction between the rigid component, namely the nasal septum, arranged medially, and the elastic component of the wing of the nose, arranged supero-laterally. It is the elastic structure that regulates the direction and flow rate of the air currents, during both inhalation and exhalation.

The area of the turbinates "nasal cavity": each nasal cavity communicates at the front with the nasal vestibule through the nasal valve and at the rear with the nasopharynx through the choanal area; medially it is delimited by the nasal septum and laterally by the lateral wall from which bony convolutions called nasal turbinates, which are covered by a highly vascularized and innervated mucosa. There are generally 3 nasal turbinates in each nasal cavity—lower, middle and upper; they are positioned between the nasal septum and the lateral wall of the nasal cavity and delimit irregular spaces called lower meatus, middle meatus and upper meatus respectively. In the upper and middle part of the nasal cavity, below the cribriform plate, the air space of which is reduced to a width of 1-2 mm, is the olfactory region, located above the middle nasal turbinate, between the nasal septum and the lateral wall. The olfactory region is covered by olfactory epithelium, present only in this region. Each nasal cavity communicates, through small ducts, with the respective paranasal sinuses: the maxillary sinuses, the frontal sinuses and the anterior ethmoid sinuses are connected to the middle meatus; the rear ethmoid sinuses and the sphenoid sinuses open into the upper meatus.

The choanal area is the terminal part of the nasal cavity through which each nasal cavity communicates with the nasopharyngeal area. The nasopharyngeal area is very important since it communicates with the cavity of the middle ear through the Eustachian tube and due to the presence of the adenoid tissue.

The nasal mucosa consists of a pseudo-stratified epithelium in which the majority of the cells are ciliated cells, caliciform cells and basal cells; the epithelium rests on a basal membrane and the latter on the plate in which capillaries, arterio-venous anastomoses, seromucous glands and cavernous sinusoids are present. The cilia are immersed in a "sol" aqueous fluid, produced by the anterior serous glands, by the seromucous glands, by the transudate of the vessels and by the condensed water of the exhaled air; on the surface there is a very thin layer of sticky mucus, a sort of "gel" produced by the caliciform cells and by the seromucous glands. The pH of the nasal mucosa is approximately 5.5-6.5. The cilia move rhythmically at a frequency of 16/sec. i.e., 1000/min., determining the movement of the mucous surface layer towards the oropharynx which, in normal conditions, takes place in approximately 12 min. (the transport speed is extremely variable from 3 to 25 mm/min.); in children the mucous is carried towards the adenoids, increasing contact with the immune system. The mucociliary system serves to humidify, warm and cleanse the inhaled air. The body temperature is ideal for the ciliary movement. The temperature influences the mucociliary system: between 32 and 40° C. the ciliary movement reaches maximum functionality and remains constant. The mucociliary system constitutes a natural barrier which has the function of protecting against pathogens and cleansing the inhaled substances.

In normal conditions the nasal cavities perform the function of conditioning the inhaled air, warming it, humidifying it and cleansing it, and the exhaled air, reabsorbing heat and humidity. The nasal turbinates make these functions possible by giving the respiratory air a turbulent motion so as to increase the surface inside the nasal cavity in contact with the air.

Prof. Niels Mygind in the paragraph dedicated to the problems of intra-nasal treatment in chapter 19 of his book "Nasal Allergy" recommends spraying the mucosa by means of a jet of pressurised liquid, in the form of spray, directed towards the upper portion (olfactory region) and towards the lower portion (lower meatus) of the nasal cavity in order to distribute the solution, administered in the form of spray, in a uniform manner inside the nasal cavity. However, Mygind's book does not provide precise anatomical references for obtaining this result; he relies solely on the personal ability of each individual to independently perform as correct a manoeuvre as possible with a dispenser having a frustoconical shape. Evidently each patient will be able to treat the pathologies of his/her nasal cavity following the teachings of "Nasal Allergy" on the condition that he/she has a detailed knowledge of the anatomy of the nasal cavity and provided that he/she is able to appropriately position and direct the apex of the dispenser inside the nasal vestibule and nasal valve.

It is expedient to point out that inappropriate manoeuvres performed by a non-expert user can damage the mucosa that covers the anterior portion of the nasal septum or the head of the lower turbinate such as, for example but not limited to, introducing the apical portion of the frustoconical dispenser too deep inside the nasal vestibule and nasal valve.

Of the known devices, the most effective ones are those produced by the applicant according to the teachings contained in its own Italian patent no. 102016000080879. The search for alternative solutions that can avoid the negative effects described has pushed the applicant to consider even more advanced embodiments of dispensers which improve distribution of the liquid in nebulized form inside the cavities to be treated and further increase the degree of turbulence of the micronized particles inside said cavities, which can be not only nasal but also oral, the outer ear canals or the vaginal cavity, to define a new standard of optimized dispensers for medical solutions which limit and overcome the drawbacks typical of the above illustrated known state of the art.

Further examples of devices according to the known art for dispensing liquids for medical purposes and/or treatments are known from the documents US 2014/121592, U.S. Pat. No. 2,266,706 and WO 2017/059405.

SUMMARY OF THE PRESENT INVENTION

The present invention concerns a dispenser according to claim 1 and a set for dispensing liquids according to at least one subsequent claim, where further embodiments of the dispenser and set according to the present invention are defined by the dependent claims. In particular, according to an embodiment described, a dispenser comprises a dome-shaped body to ease the insertion thereof in human or animal body cavities. In further detail, according to an embodiment described, a pressure-operated dispenser comprises a dome-shaped body to ease insertion in human or animal body cavities and provided with a nozzle in apical position to spray liquid in nebulized form inside the human or animal body cavities.

The object of the present invention is to provide a dispenser which is without the drawbacks described above and which, therefore, allows delivery of the liquid solutions in nebulized form so that the micronized particles of the liquid are uniformly spread and distributed on the mucosa that covers the turbinates and the walls of the nasal cavities.

According to the present invention, a simple inexpensive dispenser is provided which allows the dispensing of liquid solutions in nebulized form so that micronized particles of the liquid are uniformly spread and distributed on the mucosa that covers the turbinates and the walls of the nasal cavities.

The problems described above are solved by the present invention according to at least one of the following claims.

According to some embodiments, a dispenser of liquids for medical uses is provided in which a dome-shaped body is shaped symmetrically with respect to a first frontal median plane and to a second sagittal median plane intersected in a central axis; said dome-shaped body being developed along said axis between a base portion and an upper truncated portion provided with a cavity; at least two channels being provided, each of which accesses said cavity through a respective hole arranged at a given distance from one of said first and second planes.

According to one embodiment, said channels develop in a rectilinear manner along respective longitudinal axes and arranged on planes parallel to said second plane located on sides opposite to said central axis in order to be skew.

According to one embodiment said channels develop in a rectilinear manner along respective axes that lie on said second plane so as to be incident.

According to one embodiment a seat is provided for each said axis, where each said seat is provided with an upper part designed to house a sprayer provided with a said channel.

According to one embodiment, each said sprayer has a cylindrical portion delimited at the top by a concave portion which faces said cavity and is provided with a bottom transversal to the respective said longitudinal axis and delimited by a bevelled edge.

According to one embodiment, said cylindrical portion is contained at the bottom inside a tubular portion that covers it peripherally so as to define an axial guide for a supply duct designed to feed the respective said fluid-tight channel.

According to one embodiment said cylindrical portion has at the bottom a circular recess in hydraulic communication with the respective said channel.

According to one embodiment, each said axis is central for the respective said sprayer.

According to one embodiment said base portion has gripping means provided with at least two gripping members.

According to one embodiment, the sprayers are shaped to be interchangeable inside the respective housings.

According to one embodiment, said dome-shaped body has externally at least one discharge groove.

According to some embodiments, a liquid dispenser for medical uses is provided in which a dome-shaped body is shaped symmetrically with respect to a first frontal median plane and a second sagittal median plane intersected in a central axis; said dome-shaped body being developed along said axis between a base portion and an upper truncated portion provided with a cavity; at least one first channel and one second channel being provided, each of which extends from said base portion inside said dome-shaped body and reaches said cavity through a first hole and a second hole respectively; each of said first hole and second hole are arranged at a given distance from one of said first and second planes.

According to one embodiment, said first and second channels each develop in a rectilinear manner along a first longitudinal axis and a second longitudinal axis respectively and said first longitudinal axis and second longitudinal axis are arranged on respective planes parallel to said second plane and located on sides opposite to said central axis in order to be skew.

According to one embodiment, said first and second channels each develop in a rectilinear manner along a first longitudinal axis and a second longitudinal axis respectively which lie on said second plane so as to be incident.

According to one embodiment, a first seat and a second seat respectively, are radially symmetrical with respect to said first axis and second axis respectively, said first seat and second seat define a first upper part and a second upper part respectively, a first sprayer and a second sprayer being housed in the first upper part of said first seat and respectively in said second seat; said first sprayer and second sprayer being shaped to define said first channel and said second channel respectively.

According to one embodiment, said first sprayer and second sprayer have a first cylindrical portion and a second cylindrical portion respectively delimited at the top by a first concave portion and a second concave portion respectively which face said cavity and are each provided with a bottom transversal to said first longitudinal axis and to said second longitudinal axis respectively and delimited by a first bevelled edge and a second bevelled edge respectively.

According to one embodiment, said first cylindrical portion and second cylindrical portion are contained at the bottom inside a first tubular portion and a second tubular portion respectively which cover them peripherally so as to define a first axial guide for a first supply duct and a second axial guide for a second supply duct designed to feed said first and said second fluid-tight channels respectively.

According to one embodiment, said first cylindrical portion and second cylindrical portion have at the bottom a first circular recess and a second circular recess respectively in hydraulic communication with said first channel and said second channel respectively.

According to one embodiment, said base portion has gripping means provided with at least two gripping members.

According to one embodiment, said first sprayer and second sprayer are interchangeable inside said first seat and second seat respectively.

According to one embodiment, said dome-shaped body has externally at least one discharge groove.

According to some embodiments, a set is provided for the delivery of liquids for medical purposes and/or treatments including a distributor of pressurized liquid provided with a tank which is flexible so that it can be deformed by means of pressure exerted by a human hand and provided with a dispenser as described above.

According to one embodiment, said distributor is closed by a plug at the top of which a distributor member is arranged which splits into a first supply duct and a second supply duct, the ends of which are sized to engage by shape and in a fluid-tight manner said first sprayer and second sprayer respectively so as to feed said first sprayer and second sprayer respectively with said pressurized liquid.

BRIEF DESCRIPTION OF THE FIGURES

The invention will be better described with reference to some non-limiting embodiments in the attached figures, in which:

FIG. 9 is a lateral elevation view of a detail extracted from FIG. 1;

FIG. 10 is a longitudinal sectional view on an enlarged scale of FIG. 9;

FIG. 11 is a plan view of FIG. 9 on an enlarged scale;

FIG. 12 is a three-dimensional view of an accessory for operation of the dispenser of FIG. 1;

DETAILED DISCLOSURE OF THE PRESENT INVENTION

Figures 1, 2, 3, 4:
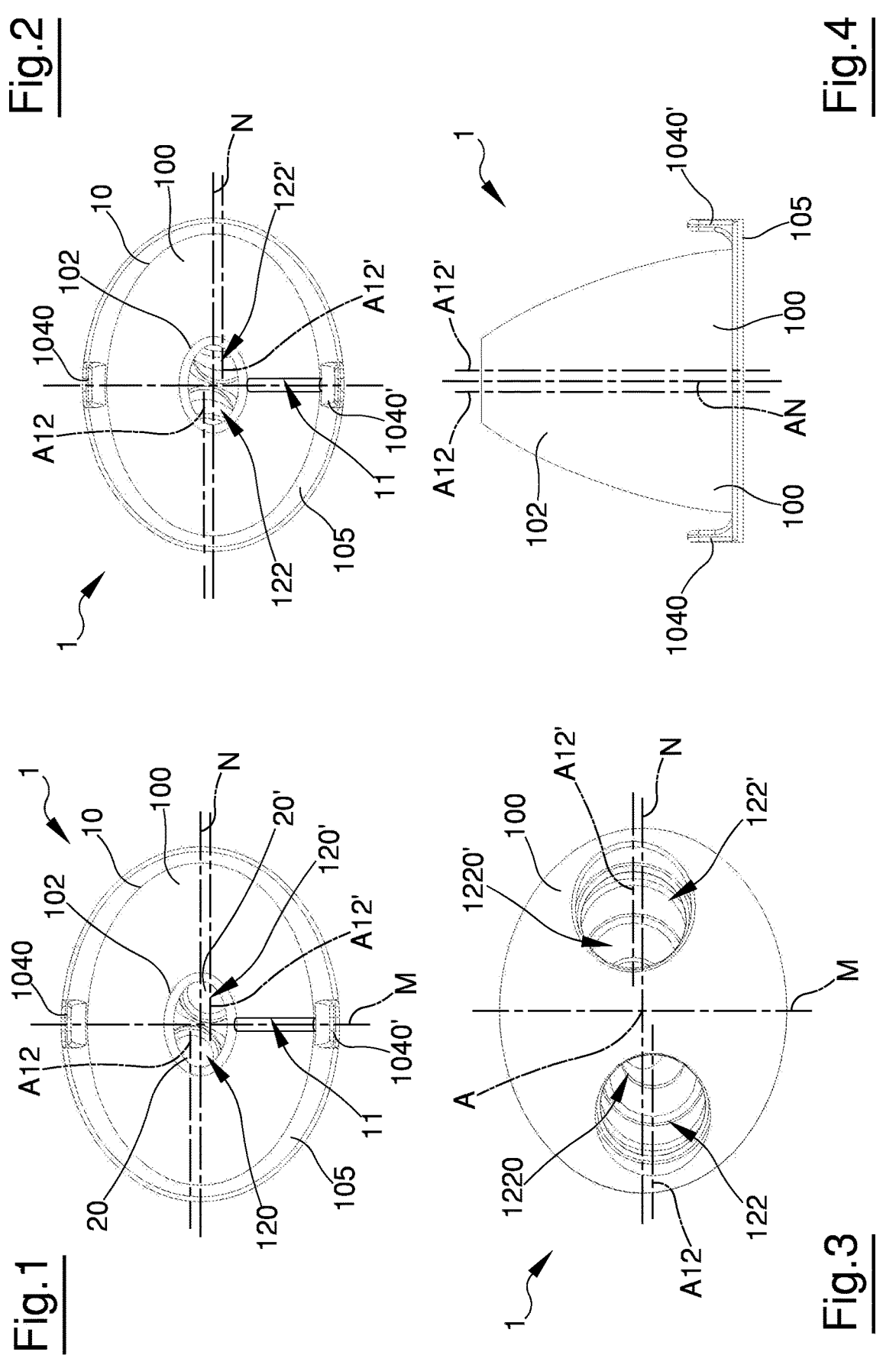
FIG. 1 is a plan view of a first preferred embodiment of a dispenser.
FIG. 2 illustrates FIG. 1 with parts removed for clarity.
FIG. 3 is a view from below of FIG. 2.
FIG. 4 is a lateral elevation view from left or right of FIG. 1.
Figures 5, 6, 7, 8:
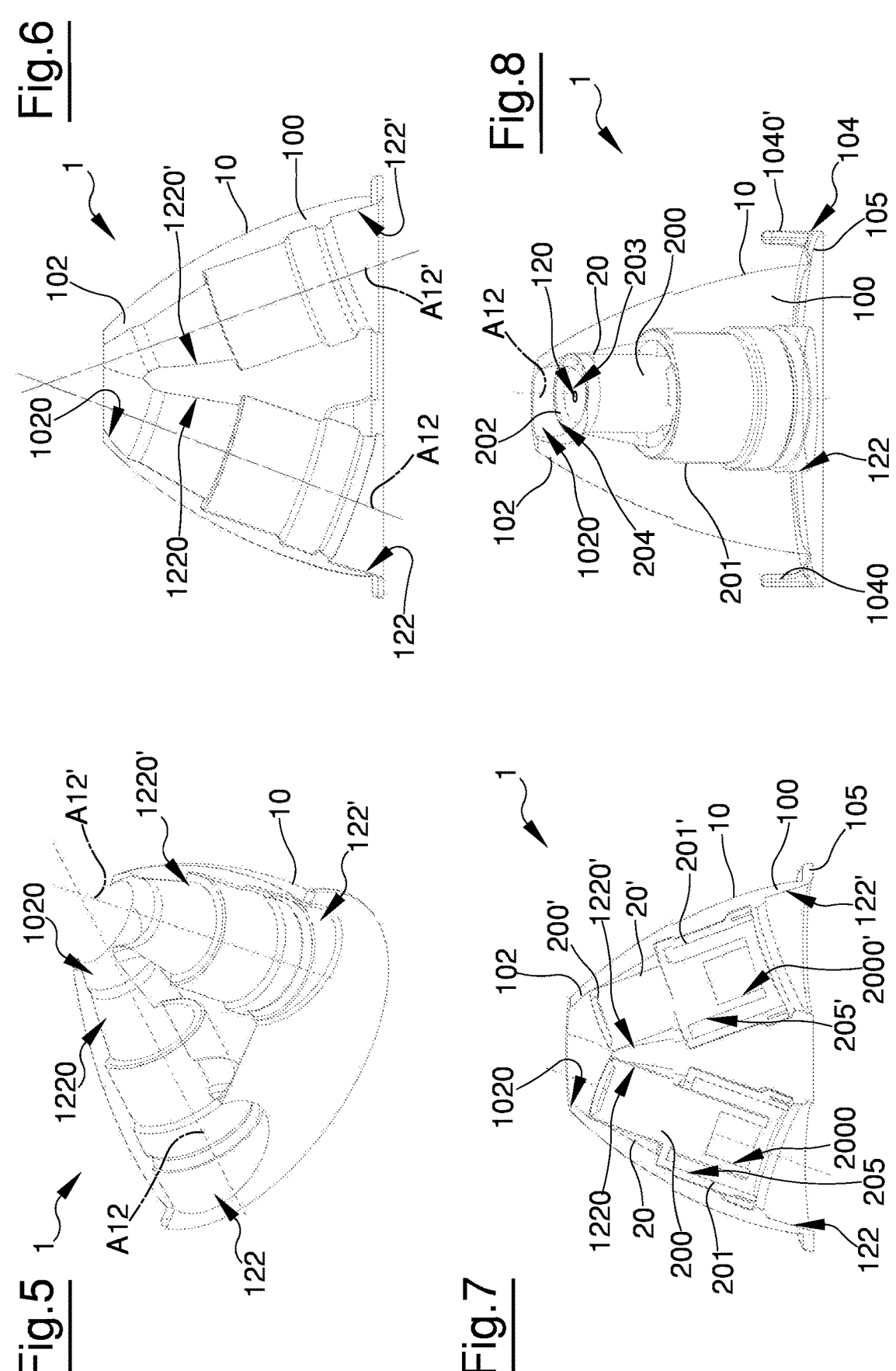
FIG. 5 is a schematic perspective view of FIG. 2 in section with a sagittal median plane.
FIG. 6 is a lateral elevation view of FIG. 5.
FIG. 7 is a lateral elevation view of a section of FIG. 1 according to said sagittal median plane.
FIG. 8 is a lateral elevation view of a section of FIG. 1 according to a median plane transversal to said sagittal median plane.

In FIG. 1, the reference number 1 indicates a liquid dispenser 1 for medical uses. It comprises a dome-shaped body 10 shaped symmetrically with respect to a first frontal median plane M and to a second sagittal median plane N intersected in a central axis A for the dome-shaped body 10. The latter is developed along the axis A between a base portion 100 and a truncated portion 102 positioned at the top and provided with a cavity 1020. Each of these median planes M and N corresponds to an axis of symmetry having given extension for the sections transversal to the central axis of said dome-shaped body 10. For this reason, the dome-shaped body 10 has an oval or elliptical cross section in each point of the respective central axis A, where the axis of symmetry corresponding to the second sagittal median plane N is greater than the axis of symmetry corresponding to the first frontal median plane M. For this reason, the dome-shaped body 10 has a shape that substantially mirrors in negative the shape of the nasal vestibule and nasal valve. This eases insertion of the dome-shaped body 10 into the nasal vestibule and nasal valve by pushing, causes adhesion of the outer wall of the dome-shaped body 10 to the inner wall of the nasal vestibule and nasal valve with univocal and appropriate orientation of said dome-shaped body 10 and allows widening of the inner wall of the vestibule and valve in a physiologically compatible manner. Further to the above description, the dome-shaped body 10 is shaped in a manner compatible with the nostrils.

With particular reference to FIGS. 3, 5-8 the dispenser 1 has at least one pair of seats 122 and 122' having substantially identical geometrical shape which develop in an axially symmetrical manner along the respective axes A12 and A12', which are arranged on planes parallel and symmetrical to the second sagittal median plane N, therefore on sides opposite to a major axis of a section of the dome-shaped body 10 transversal to the central axis A and thus located on sides opposite the central axis A in order to be skew.

With particular reference to FIGS. 5-8, each seat 122/122' is provided with a respective upper part 1220/1220' designed to house a sprayer 20/20' (FIGS. 7-10) provided with a channel 12/12'. Each sprayer 20/20' furthermore has a cylindrical portion 200/200' which is delimited at the top by a concave portion 202/202', which faces the cavity 1020, is provided with a bottom 203/203' transversal to the respective longitudinal axis A12/A12', the reference of which is, for the sake of practicality, the same as that of the longitudinal axes of the seats 122 and 122' which house the sprayers 20/20' respectively. Each bottom 203 and 203' is peripherally delimited by a bevelled edge 204/204'. From FIG. 7 it can be seen that each of the two channels 12/12' accesses the cavity 1020 through a respective hole 120/120' arranged at a given distance from one of the first frontal median plane M and second sagittal median plane N. In addition, as shown in FIGS. 7-10, each axis A12/A12' is central for the respective sprayer 20/20' and the channels 12/12' develop in a rectilinear manner along the respective axes A12 and A12'. Further to the above description, the channels 12 and 12' are skew and, therefore, the respective ideal extensions do not cross. With particular reference to FIG. 10, the cylindrical portion 200/200' is contained at the bottom inside a tubular portion 201/201' which covers it peripherally thus defining an axial cylindrical guide 205/205' for a supply duct designed to feed the respective fluid-tight channel 12/12' which will be better described below. Furthermore, the cylindrical portion 200/200' has at the bottom a circular recess 2000/2000' in hydraulic communication with the respective channel 12/12', therefore with the cavity 1020. With particular reference to FIG. 12, a liquid distributor 40 is shown which is provided with a substantially cylindrical tank 41 having dimensions that can be gripped by a human hand, where the peripheral wall 42 of the tank 41 is flexible so that it can be deformed by pressure that can be radially exerted by a human hand. Said distributor 40 is closed by a plug 43 at the top of which a distributor member 45 is arranged which splits into two cylindrical section supply ducts 47/47', the end of which is sized to engage by shape and in a fluid-tight manner each sprayer 20/20' inside the respective cylindrical guide 205/205', so as to supply the dispenser 1 with pressurized liquid, where the pressure is the result of a radial compression exerted on the wall 42 of the distributor 40.

With reference to FIGS. 1-4 and 8, the base portion 100 has a gripping device 104 (FIG. 8) defined by a peripheral flat portion 105 which is provided with at least two gripping members 1040/1040' positioned symmetrically with respect to the second sagittal median plane N and centred on the first frontal median plane M.

The use of the dispenser 1 can be easily understood from the above description and does not require further explanation. However, it may be useful to specify that when the adhesion of the outer wall of the dome-shaped body 10 to the inner wall of the nasal vestibule and nasal valve has been determined by pushing in a physiologically correct manner, and the dome-shaped body 10 is held firm in said position, the dispenser 1 can spray medical liquid simultaneously to the lower, middle and upper meatus of the nasal cavities through the channels 12 and 12'. The resulting widening of the inner walls of the nasal vestibule and nasal valve allows positioning of the apex of the dispenser, and with it the holes 120 and 120' of the sprayers 20 and 20', at the beginning of the nasal cavity, inside which are the turbinates, and delivery of the medical liquid in nebulized form through the channels 12 and 12' in accordance with Bernoulli's equation, always in the same direction inside the nasal cavity, namely towards the three meatus—lower, middle and upper—and the air space between the wall of the nasal septum and the turbinates. Therefore any person, even without knowing the physiology of the nasal cavities, can perform this operation accurately and correctly using the dispenser 1 since the convex part of the dome-shaped body 10 is designed to occupy the entire inner area of the nasal vestibule and nasal valve giving rise to a standardized reference, which validates the hypothesis of Prof. Niels Mygind, originally lacking said precondition. It is useful to specify that the dome-shaped body 10 has externally at least one groove 11, the function of which is to discharge excess air or liquid from the nasal cavity so that the liquid nebulized by the sprayers 20/20' inside the cavity 1020 is diffused as deeply as possible inside the nasal cavity, and prevent any increase in pressure during administration of the nebulized solution or solution in the form of spray or aerosol. FIGS. 1 and 2 show only one groove 11 for the sake of practicality, without conditioning the scope of the present invention.

Obviously the fact of considering the liquid distributor 40 provided with the substantially cylindrical tank 41 and having dimensions that can be gripped by a human hand does not aim to limit the scope of the present invention and therefore any device designed to pressurize liquid and supply it to the sprayers 20 and 20', which can be operated manually or in any other way, falls within the scope of the present invention.

The patent no. 102016000080879 of the applicant cited above should be referred to, in particular a liquid that passes through a small-diameter channel, like the channels 12 and 12', which open into a cavity like the cavity 1020 described above, open at the top and delimited by the bottoms 203 and 203' of the sprayers 20 and 20', is nebulized, namely broken down into particles which are deviated and distributed in all directions and in a turbulent manner above the holes 120 and 120', therefore also circumferentially with respect to the relative axes.

Considering that in this case the channels 12 and 12' are rectilinear and skew, the pressure exerted on the wall 42 of the distributor 40 supplies pressurized liquid to the holes 120 and 120' of the sprayers 20 and 20' determining the formation of clouds of liquid particles. Said particle clouds are spread in a swirling manner across the first frontal median plane M and from the two sides of the second sagittal median plane N, therefore parts of them are reciprocally facing around the axis A so that they inevitably collide. The effect of this collision is an increase in the turbulence of said particles, which causes an increase in the uniformity of distribution of the particles inside the nasal cavity, the mucosa of which are uniformly sprayed by the pressurized liquid inside the nasal cavity, including the mucosa that covers the nasal cavity from the olfactory region to the lower meatus. Therefore, due to the particular structural combination in which the sprayers 20 and 20' are inserted, due to the presence of the cavity 1020 to which the channels 12 and 12' lead, the dispenser 1 can be said to be a nebulizer. It should be specified that to obtain an effective turbulence of the liquid particles to be delivered into the body/nasal cavities, the number of sprayers 20/20' required must necessarily be more than one, but said number can also be greater than two without modifying the scope of the present invention. Naturally, coherently with the above description, the longitudinal axes A12/A12' (and A12" of the additional channels 12") must be arranged in a radial pattern around the axis A so that they are skew two by two, maximizing the capacity to interfere between the jets of liquid delivered by each channel and therefore the degree of nebulization of the liquid.

Lastly it is clear that variations can be made to the dispenser 1 described and illustrated above without departing from the scope of the present invention, in which identical or corresponding parts of the modified versions will be identified by the same reference numbers, unless indicated otherwise.

Figures 13, 14, 15:
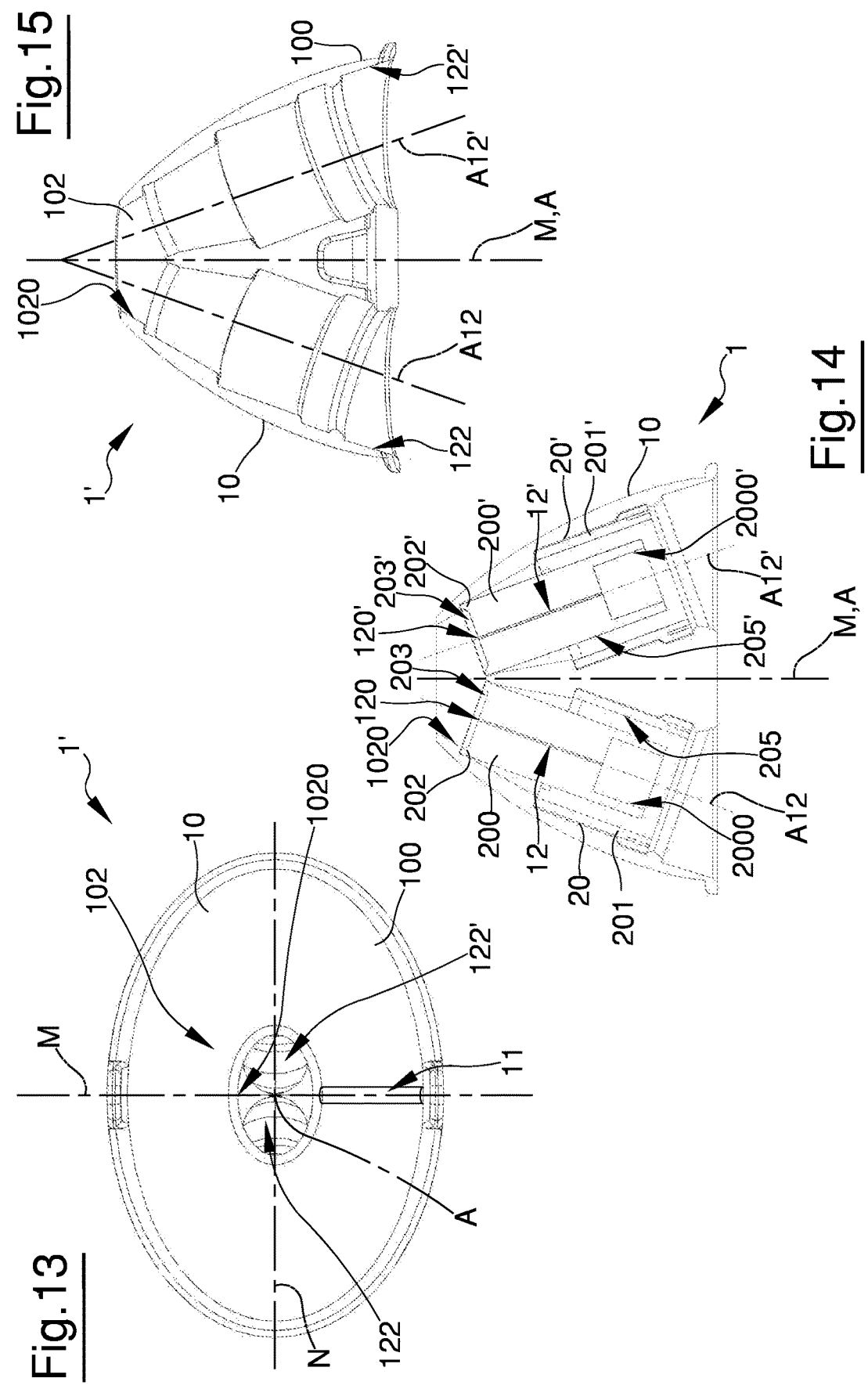
FIG. 13 is a plan view showing a section from above of a second preferred embodiment of FIG. 1.
FIG. 14 is a lateral elevation view of a section of FIG. 13 according to a sagittal median plane.
FIG. 15 illustrates FIG. 13 with details removed for clarity.

For example, with reference to FIGS. 13-15, to maximize dispersion of the liquid particles delivered by a modified dispenser 1', provided with only two sprayers 20/20', the seats 122/122' are constructed so that the sprayers 20 and 20' have the respective channels 12/12' developed along respective axes A12/A12' which are incident, since they share the position in which they lie coinciding with the second sagittal median plane N; this maximizes the aliquot part of nebulized particles, therefore increasing the turbulence of the liquid broken down into particles inside the body/nasal cavities and maximizing effectiveness of the delivery. In this case, in fact, all the particles of the jet delivered by each of the sprayers 20/20' are diffused towards one another, crossing within the axis A above the dome-shaped body 10. Since each particle of liquid corresponding to each jet is potentially involved in collision with one of the particles of the other jet, the resulting turbulence of the jet is maximum and, therefore, distribution of the nebulized liquid particles is uniform throughout the nasal cavity.

It may be useful to specify that the sprayers 20 and 20' are shaped to be interchangeable within the respective housings.

Further to the above description, it can be seen that a dispenser shaped like the dispenser 1' and therefore provided with at least two sprayers 20/20', each provided with a channel 12/12' which ends in a cavity 1020 with respective holes 120 and 120', are designed to maximize the degree of turbulence of the liquid particles supplied by the distributor 40 since said particles are induced to cross one another, both when the axes A12 and A12' are skew and when they are incident, therefore maximizing the surface area of the mucosa sprayed from the floor of the lower meatus to the upper meatus in the olfactory area.

The invention claimed is:

1. A liquid nebulizer for medical uses wherein a dome-shaped body is shaped symmetrically with respect to a first frontal median plane and to a second sagittal median plane intersected in a central axis; said dome-shaped body being developed along said axis between a base portion and an upper truncated portion provided with a cavity; wherein said dome-shaped body has at least a first channel defined within a first sprayer and a second channel defined within a second sprayer, each of which extends from said base portion inside said dome-shaped body and leads into said cavity through a first hole and a second hole respectively, and in that each of said first hole and second hole is arranged at a given distance from one of said first frontal median plane and second sagittal median plane; each of said first channel and said second channel terminating prior to a bottom surface of the base portion, wherein said first channel and second channel each develop in a rectilinear direction along a first longitudinal axis and a second longitudinal axis respectively; said first channel and second channel being arranged on respective planes parallel to said second sagittal median plane and located on sides opposite to said central axis in order to be skew or being arranged on respective planes which lie on said second sagittal median plane in order to be incident.

2. The nebulizer according to claim 1, further comprising a first seat and a second seat respectively, radially symmetrical with respect to said first axis and second axis respectively, in that said first seat and second seat define a first upper part and a second upper part respectively, wherein the first sprayer and the second sprayer are housed in the first upper part of said first seat and respectively in said second seat; wherein said first sprayer and second sprayer have a first cylindrical portion and a second cylindrical portion respectively, the first cylindrical portion and the second cylindrical portion terminating at locations that are spaced from and are above the bottom of the base portion.

3. The nebulizer according to claim 2, wherein the first cylindrical portion and the second cylindrical portion respectively, are delimited at the top by a first concave portion and a second concave portion respectively which face said cavity and are each provided with a bottom transversal to said first longitudinal axis and to the second longitudinal axis respectively, and delimited by a first beveled edge and a second beveled edge respectively.

4. The nebulizer according to claim 3, wherein said first cylindrical portion and second cylindrical portion are contained at the bottom inside a first tubular portion and a second tubular portion respectively, which cover them peripherally so as to define a first axial guide for a first supply duct and a second axial guide for a second supply duct designed to feed said first and said second channels, respectively.

5. The nebulizer according to claim 4, wherein said first cylindrical portion and second cylindrical portion have at the bottom a first circular recess and a second circular recess respectively, in hydraulic communication with said first channel and said second channel respectively.

6. The nebulizer according to claim 2, wherein said first sprayer and second sprayer are interchangeable inside said first seat and second seat respectively.

7. The nebulizer according to claim 1, wherein said base portion has gripping means provided with at least two gripping members.

8. The nebulizer according to claim 1, wherein said dome-shaped body has externally at least one discharge groove.

9. A set for dispensing liquids for medical purposes and/or treatments inclusive of a pressurized liquid distributor provided with a tank which is flexible so that it can be deformed by means of pressure that can be exerted by a human hand, characterized in that it comprises a nebulizer according to claim 1.

10. The set according to claim 9, wherein said distributor is closed by a plug at the top of which a distributor member is arranged which splits into a first supply duct and a second supply duct, the ends of which are sized to engage by shape and in a fluid-tight manner said first sprayer and second sprayer respectively so as to feed said first sprayer and second sprayer respectively with said pressurized liquid.

11. A liquid nebulizer for medical uses wherein a dome-shaped body is shaped symmetrically with respect to a first frontal median plane and to a second sagittal median plane intersected in a central axis; said dome-shaped body being developed along said axis between a base portion and an upper truncated portion provided with a cavity; wherein said dome-shaped body has at least a first channel defined within a first sprayer and a second channel defined within a second sprayer, each of which extends from said base portion inside said dome-shaped body and leads into said cavity through a first hole and a second hole respectively, and in that each of said first hole and second hole is arranged at a given distance from one of said first frontal median plane and second sagittal median plane; wherein said first channel and second channel each develop in a rectilinear direction along a first longitudinal axis and a second longitudinal axis respectively; said first channel and second channel being arranged on respective planes parallel to said second sagittal median plane and located on sides opposite to said central axis in order to be skew or being arranged on respective planes which lie on said second sagittal median plane in order to be incident;

wherein said first sprayer and second sprayer have a first cylindrical portion and a second cylindrical portion respectively;

wherein said first cylindrical portion and second cylindrical portion have at the bottom a first circular recess and a second circular recess respectively, in hydraulic communication with said first channel and said second channel respectively;

wherein the first cylindrical portion and the second cylindrical portion are contained at the bottom inside a first tubular portion and a second tubular portion respectively, with the first tubular portion extending below the first cylindrical portion and the second tubular portion extending below the second cylindrical portion;

wherein a first axial guide is defined between the bottom of the first cylindrical portion and the first tubular portion such that the first axial guide is open along a bottom of the first sprayer and is in communication with the first circular recess, the first axial guide configured to receive a first supply duct for feeding said first channel through the first circular recess; and wherein a second axial guide is defined between the bottom of the second cylindrical portion and the second tubular portion such that the second axial guide is open along a bottom of the second sprayer and is in communication with the second circular recess, the second axial guide configured to receive a second supply duct for feeding said second channel through the first circular recess.

12. The nebulizer according to claim 11, wherein the first axial guide has a height that is greater than a height of the first circular recess and the second axial guide has a height that is greater than a height of the second circular recess.

13. The nebulizer according to claim 11, wherein the first axial guide annularly surrounds the first cylindrical portion and extends to a location above a top of the first circular recess and the second axial guide annularly surrounds the second cylindrical portion and extends to a location above a top of the second circular recess.

14. The nebulizer according to claim 11, further including a first seat and a second seat respectively, radially symmetrical with respect to said first axis and second axis respectively, in that said first seat and second seat define a first upper part and a second upper part respectively, with the first sprayer housed in the first upper part of the first seat and the second sprayer housed in the second upper part of the second seat, the first circular recess and the bottom of the first sprayer being above a bottom open cavity of the first seat that terminates at a bottom of the base portion, the second circular recess and the bottom of the second sprayer being above a bottom open cavity of the second seat that terminates at the bottom of the base portion.

15. The nebulizer according to claim 11, wherein the first cylindrical portion and the second cylindrical portion terminate at locations that are spaced from and are above the bottom of the base portion.

\* \* \* \* \*